United States Patent
Thibos et al.

(10) Patent No.: US 8,591,032 B2
(45) Date of Patent: Nov. 26, 2013

(54) OPTHALMIC APPARATUSES, SYSTEMS AND METHODS

(75) Inventors: Larry N. Thibos, Bloomington, IN (US); Xin Wei, Houston, TX (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 122 days.

(21) Appl. No.: 12/987,504

(22) Filed: Jan. 10, 2011

(65) Prior Publication Data

US 2011/0211162 A1    Sep. 1, 2011

Related U.S. Application Data

(63) Continuation of application No. PCT/US2009/002696, filed on May 1, 2009.

(60) Provisional application No. 61/134,492, filed on Jul. 10, 2008, provisional application No. 61/092,096, filed on Aug. 27, 2008.

(51) Int. Cl.
  *A61B 3/10* (2006.01)
(52) U.S. Cl.
  USPC .......................................... 351/221; 351/205
(58) Field of Classification Search
  USPC ................. 351/205, 206, 215, 221, 246, 247;
  600/557, 318–321, 473, 476;
  356/124–127
  See application file for complete search history.

(56) References Cited

U.S. PATENT DOCUMENTS

| | | | |
|---|---|---|---|
| 5,706,073 A | 1/1998 | Volk | |
| 5,815,242 A | 9/1998 | Anderson et al. | |
| 6,112,114 A * | 8/2000 | Dreher | 600/476 |
| 6,271,915 B1 | 8/2001 | Frey et al. | |
| 6,299,311 B1 * | 10/2001 | Williams et al. | 351/221 |
| 6,497,483 B2 | 12/2002 | Frey et al. | |
| 6,634,750 B2 * | 10/2003 | Neal et al. | 351/211 |
| 7,025,460 B2 | 4/2006 | Smitth et al. | |
| 7,029,117 B2 | 4/2006 | Suzaki et al. | |
| 7,044,944 B2 | 5/2006 | Campin et al. | |
| 7,303,281 B2 | 12/2007 | Wakil et al. | |
| 7,891,812 B2 * | 2/2011 | Larichev et al. | 351/211 |
| 2002/0097492 A1 | 7/2002 | Cobb et al. | |
| 2003/0053028 A1 * | 3/2003 | Wirth | 351/221 |
| 2003/0117581 A1 * | 6/2003 | Martino et al. | 351/221 |
| 2003/0193647 A1 * | 10/2003 | Neal et al. | 351/221 |

(Continued)

OTHER PUBLICATIONS

Porter et. al. "Strategies for High-Resolution Retinal Imaging." 2006. Wiley. 235-237.*

(Continued)

*Primary Examiner* — Thomas K Pham
*Assistant Examiner* — William M Johnson
(74) *Attorney, Agent, or Firm* — Krieg DeVault LLP (57) ABSTRACT

Ophthalmic apparatuses, systems and methods are disclosed. One embodiment is an ophthalmic scanning apparatus including a laser operable to emit a laser beam, a scanning mirror operable to scan the laser beam over at least a +/−15 degree scan, and a lens system operable to receive the laser beam from the scanning mirror and direct the laser beam to a spot on an image plane. The spot has a root mean square radius of less than about 3.8 microns over the +/−15 degree scan. Further embodiments include methods of modeling and determining corrective prescriptions for patient's eyes. Additional embodiments are described herein.

20 Claims, 9 Drawing Sheets

(56) References Cited

U.S. PATENT DOCUMENTS

| | | |
|---|---|---|
| 2003/0231285 A1 | 12/2003 | Ferguson |
| 2006/0203195 A1 | 9/2006 | Squire et al. |
| 2007/0091257 A1 | 4/2007 | Spivey |
| 2007/0252951 A1* | 11/2007 | Hammer et al. ............. 351/221 |
| 2007/0291230 A1* | 12/2007 | Yamaguchi et al. .......... 351/221 |
| 2008/0218694 A1* | 9/2008 | Chen et al. .................... 351/206 |
| 2009/0009717 A1* | 1/2009 | Barrett et al. ................. 351/221 |

OTHER PUBLICATIONS

ISA/US, International Search Report and Written Opinon, Sep. 28, 2009, International Application No. PCT/US2009/002696, Indiana University Research & Technology Corporation.

Xin Wei and Larry Thibos, Modeling the eye's optical system by ocular wavefront tomography, School of Optometry, Indiana University, Nov. 25, 2008, Optical Society of America, vol. 16, No. 25.

Extended European Search Report, Oct. 9, 2012, EP 09794754, PCT/US2009002696, European Patent Office, Munich.

* cited by examiner

OPTHALMIC APPARATUSES, SYSTEMS AND METHODS

CROSS REFERENCE

The present application is a continuation of International Patent Application No. PCT/US2009/002696, filed on May 1, 2009, which claims the benefit of U.S. Patent Application No. 61/134,492, filed on Jul. 10, 2008, and U.S. Patent Application No. 61/092,096, filed on Aug. 27, 2008, all of which are hereby incorporated by reference and the benefit of all of which is claimed.

GOVERNMENT RIGHTS

This invention was made with Government support under National Institutes of Health Grant No. R01-EY05109. The Government has certain rights in the invention.

TECHNICAL FIELD

The technical field relates generally to ophthalmic apparatuses, systems and methods, and more particularly but not exclusively to apparatuses, systems and methods for measuring ophthalmic aberration and determining ophthalmic prescriptions.

BACKGROUND

Human beings depend on peripheral vision in a number of important visual tasks such as locomotion and driving. These activities are limited by the optical quality in the peripheral visual field. Peripheral optical quality is also implicated in emmetropization and myopia development. The optical quality of the eye also limits diagnostic imaging of the retina which is needed to detect disease. At the same time the human beings also highly depend on the central visual field in performing a number of important visual tasks. Present approaches to measuring ophthalmic aberration and determining ophthalmic prescriptions suffer from significant limitations relating to the peripheral visual field as well as the central visual field. There is a need for the unique and inventive ophthalmic apparatuses, systems and methods disclosed herein.

DETAILED DESCRIPTION

For purposes of promoting an understanding of the principles of the invention, reference will now be made to the embodiments illustrated in the figures and specific language will be used to describe the same. It will nevertheless be understood that no limitation of the scope of the invention is thereby created, and that the invention includes and protects such alterations and modifications to the illustrated embodiments, and such further applications of the principles of the invention illustrated therein as would occur to one skilled in the art to which the invention relates.

Figure 1:
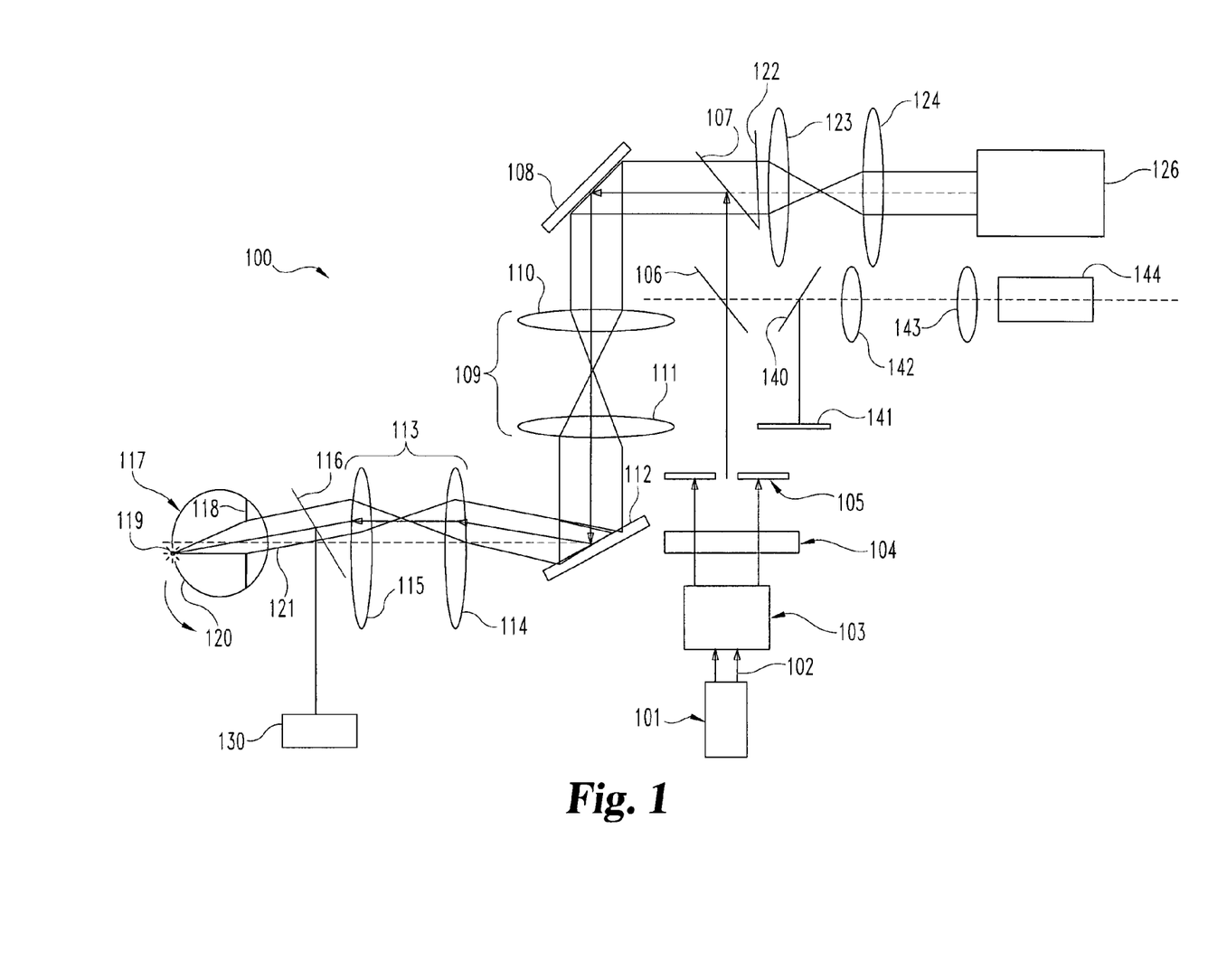
FIG. 1 illustrates an exemplary scanning Hartmann Shack wavefront sensor system.

FIG. 1 illustrates an exemplary scanning Hartmann Shack wavefront sensor system 100. System 100 is operable to progressively measure the off-axis wavefront aberrations of the human eye over a large filed of view. In various embodiments the field of view can be +/−15 degrees or greater, +/−30 degrees or greater, +/−45 degrees or greater, or +/−50 degrees or greater.

System 100 includes laser 101 which outputs a laser beam 102. While laser beam 102 is subsequently split, apertured, filtered or otherwise subject to treatment which divides it into portions, for clarity of description such portions are referred to as laser beam 102. Laser beam 102 is expanded by beam expander 103 and filtered by filter 104 which can be a polarizing filter or a graduated neutral filter, or both. Laser beam 102 passes through aperture 105, beam splitter 106, beam splitter 107, and is directed to horizontal scanning mirror 108. From horizontal scanning mirror 108, laser beam 102 passes through relay telescope pair 109 which includes double pass scanning ("DPS") lens 110 and DPS lens 111. From relay telescope pair 109, laser beam 102 passes to vertical scanning mirror 112. From vertical scanning mirror 112, laser beam 102 passes through relay telescope pair 111 which includes DPS lens 114 and DPS lens 115. From relay telescope 113 laser beam 102 passes through beam splitter, to a spot on the pupil plane of eye 117, into eye 117 through the aperture of iris 118 and to a spot 119 on retina 120.

Reflected light from spot 119 on retina 120 exits eye 117, through the aperture of iris 118 and proceeds along wavefront pathway 121. Wavefront pathway 121 passes through DPS lens 115 and DPS lens 114 of relay telescope pair 113 to vertical scanning mirror 112. From vertical scanning mirror 112 wavefront pathway 121 passes though DPS lens 111 and DPS lens 110 of relay telescope pair 109 and to horizontal scanning mirror 108. From horizontal scanning mirror 108, wavefront pathway 121 passes through cross polarizer 122, lens 123, lens 124 and to Hartmann Shack wavefront sensor 126. The reflected wavefront is sampled by a lenslet array on a sensor plane of sensor 126. Sensor 126 can pass sensed information to one or more computer-based processing systems. Scanning mirrors 108 and 112 are operable to vary the scanning angle of laser beam 102 in the horizontal and vertical directions. For off-axis scanning angles or lines of sight the optical axis of the patient's eye is oblique to the optical axis of the lenslet array and the pupil information sensed by the sensor 126 has an irregular shape such as elliptical or oval.

System 100 is one example of an ophthalmic double pass scanning system. Ophthalmic double pass scanning includes a number of optical scanning techniques in which scanning light is passed through an optical system in one direction, and reflected or scattered light returns through the optical system in the opposite direction. For example, system 100 on the first pass scans a narrow laser beam through a scanning range including the peripheral visual field of a patient's eye. In the first pass (scanning pass), the DPS lenses minimize on-axis aberration within a large aperture. This provides effective conjugation of the scanning center and the center of the entrance pupil over a large visual field. In the second pass (reflected pass), a wavefront emerging from the patient's pupil passes through system 100 in the reverse direction as the scanning pass. The DPS lenses minimizes the aberration introduced by the system at all scanning angles as well as aberrations in the return scan in a large field of view. Relay telescope pair 109 which includes DPS lens 110 and DPS lens 111 lens conjugates the rotation axis of horizontal mirror 108 to the rotation axis of vertical mirror 112. Relay telescope pair 113 which includes DPS lens 115 and DPS lens 114 conjugates the rotation axis of the vertical mirror 113 to the center of entrance pupil 118. In this design. DPS lenses 110,111, 114, and 115 are substantially the same. Doublet lenses can be used for lens 123 and lens 124.

Some embodiments include alternate or additional sensors such as curvature sensors, Hartmann-Moiré wavefront sensor, various interferometers, diffraction wavefront sensors. Some embodiments employ DPS lenses and/or additional features of system 100 in instruments such as scanning laser ophthalmoscopes, scanning fundus cameras, nerve fiber analyzers, optical coherence tomography systems, or retina imaging instruments such as laser ray tracing instruments and point spread function cameras. In some embodiments the scanning directions of scanning mirrors 108 and 112 are reversed. Some embodiments include polar scanning schemes or scanning schemes of geometries other than x-y scanning schemes. Some embodiments include a multi-axial scanning mirror in place of the horizontal and vertical scanning mirrors effective to scan in both horizontally and vertically or in accordance with polar or other scanning schemes. Some embodiments include alternate or additional DPS systems and/or alternate or additional DPS elements. In some embodiments the DPS functionality of one or more of DPS lenses 110, 111, 114, and 115 can be performed by one or more mirrors effective to achieve substantially the same or similar DPS qualities. Some embodiments use DPS mirrors instead of DPS lenses. Some embodiments use combinations of DPS lenses and DPS mirrors.

A number of additional features may be provided to enhance the performance of system 100. For example, peripheral fixation targets such as target 130 can be used to provide an optical image upon which a patient is instructed to focus can be used. A Badal system (not illustrated) can be introduced to adjust the distance between DPS lens 114 and DPS lens 115 of relay telescope pair 111 in order to effectively enlarge the detecting range for defocus. Cross polarizers and limiting apertures (not illustrated) placed at the foci plane of lens 123 and lens 124 may effectively reduce the backward scattering of the system and enhance the robustness (signal-to-noise ratio) of system 100. Pupil camera 144, beam splitter 140, lenses 142 and 143, and alignment ring 141 can be used for corneal Purkinje images to ensure a good alignment of the subject's eye with the instrumentation. These and other additional or alternate features may be present in various embodiments.

Figure 2:
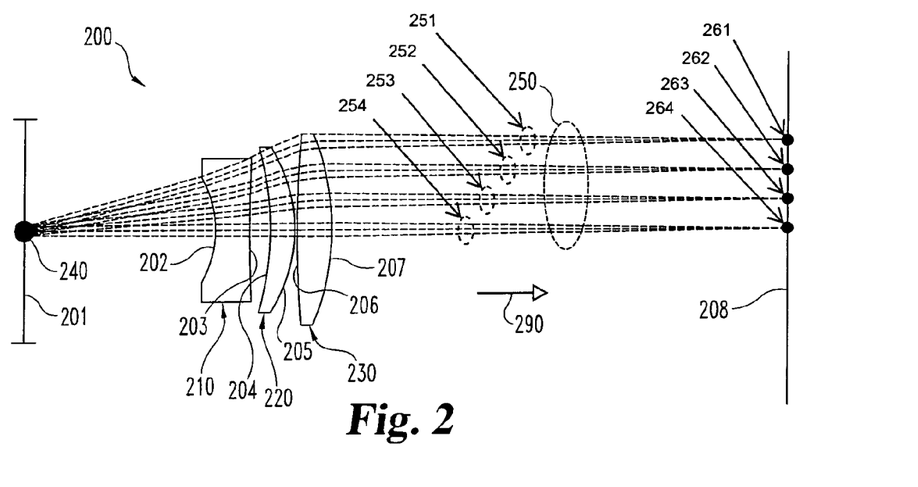
FIG. 2 illustrates an exemplary reflection pass of an exemplary double pass scanning lens system.

FIG. 2 illustrates an exemplary reflection pass of an exemplary double pass scanning ("DPS") lens system 200 which includes lens 210, lens 220 and lens 230. DPS lens system 200 is designed to optimize scanning performance in one direction and optimize on-axis performance over a large aperture in the reverse direction.

These design features minimize systematic errors over a large visual field and permits improved measurement of off-axis wavefront aberration over a large visual filed. Detailed characteristics of DPS lens system 200 are listed in Tables 1, 2, and 3 below.

TABLE 1

| Surface No. | Radius of Curvature (mm)/ Corresponding Test Plate No. | Distance to Next Surface No. (mm) | Medium/ Refractive Index | Clear Aperture Diameter (mm) |
|---|---|---|---|---|
| 201 | Infinity | 112.41 | Entrance Pupil | 6 |
| 202 | −60.985/T#251 | 20.00 | S-BSL7/ 1.509562 | 61.8 |
| 203 | 1411.224/T#575 | 11.52 | Air | 83.2 |
| 204 | −172.949/T#380 | 13.84 | S-TIH11/ 1.762466 | 89.6 |
| 205 | −93.929/T#305 | 1.50 | Air | 95.8 |
| 206 | 587.731/T#509 | 20.00 | S-TIH11/ 1.762466 | 108.6 |
| 207 | −151.587/T#360 | 262.34 | Air | 110.0 |
| 208 | Infinity | 0 | Image Plane | 102.8 |

TABLE 2

| | |
|---|---|
| Equivalent or Effective Focal Length | 195.02 mm |
| Front Vertex Distance (distance from vertex of the first optical surface to the image plane). | 441.61 mm |
| Barrel Length (distance first glass vertex to the last vertex) | 66.86 mm |
| Back Focal Length | 262.34 mm |
| F Number of the Lens | 32.50 |
| Field of View | +/−15 degrees |
| Spectrum (designed working wavelength of lens) | 840 nm |

TABLE 3

Tolerance Report

| | |
|---|---|
| Radius Tolerance of Surface 2 | 0.05% Testplate Accuracy |
| Radius Tolerance of Surface 203 | 0.1% Testplate Accuracy |
| Radius Tolerance of Surface 204 | 0.1% Testplate Accuracy |
| Radius Tolerance of Surface 205 | 0.05% Testplate Accuracy |
| Radius Tolerance of Surface 206 | 0.1% Testplate Accuracy |
| Radius Tolerance of Surface 207 | 0.05% Testplate Accuracy |
| Surface Irregularity | 0.5 fringe across the overall clear aperture @ 546.1 nm |
| Surface Quality | 60/40 |

TABLE 3-continued

Tolerance Report

| | |
|---|---|
| Thickness of Lens 210 | 0.025 mm |
| Thickness of Lens 220 | 0.050 mm |
| Thickness of Lens 230 | 0.050 mm |
| Thickness of Space Between Lens 210 and 220 | 0.05 mm |
| Air Thickness of Space Between Lens 210 and 220 | 0.025 mm |
| Tilt of Lens 210 | 0.010 degrees |
| Tilt of Lens 220 | 0.020 degrees |
| Tilt of Lens 230 | 0.025 degrees |
| Decentration of all Lenses | 0.03 mm |
| Wedge of all Lenses | 0.010 mm |
| Tilt of Surface Nos. 202, 204 and 205 | 0.020 degrees |
| Tilt of Surface Nos. 203 and 207 | 0.015 degrees |
| Tilt of Surface No. 206 | 0.010 degrees |
| Wedge Tilt of Surface Nos. 204 and 205 | 0.030 mm |
| Wedge Tilt of Surface Nos. 202, 203 and 207 | 0.020 mm |
| Wedge Tilt of Surface No. 206 | 0.015 mm |
| Decentration of Surface Nos. 203, 204 and 206 | 0.05 mm |
| Decentration of Surface Nos. 202, 205 and 207 | 0.03 mm |
| Refractive Index | 0.0005 |
| Material Quality | Standard |
| Homogeneity | 0.00003 |
| Coating | Broad Band AR |

In Tables 1, 2 and 3 above, surface irregularity was evaluated using the formula OPD=0.5(n'−n)N where OPD was the wavelength deformation in wave, n'−n is the index change, and N is the fringe number. In the foregoing data wedge was converted from the tilt angle by the formula $\Delta y=\theta_x \times d$ where $\theta_x$ is the change in angle for tilt along x in unit; radians and d is the diameter of clear aperture.

FIG. 2 illustrates a reflected light wavefront 250 including pluralities of rays at various angles (labeled 251, 252, 253, and 254) emerging from a patients pupil 240 on pupil plane 201 and traveling generally in the direction indicated by arrow 290. Lens 210, 220, and 230 are operable to direct the wavefront including rays 251, 252, 253, and 254 from the patients pupil 240 to spots 261, 262, 263, and 264 on image plane, respectively. Lens system 200 is operable to produce image spots 261, 262, 263, and 264 with the characteristics described below in Table 4.

| Rays | OBJ | IMA | RMS | GEO |
|---|---|---|---|---|
| 254 | 0 degrees | 0 mm | 1.320 microns | 1.537 microns |
| 253 | 5 degrees | 17.028 mm | 2.192 microns | 5.838 microns |
| 252 | 10 degrees | 34.135 mm | 3.801 microns | 9.493 microns |
| 251 | 15 degrees | 51.393 mm | 2.809 microns | 6.543 microns |

In Table 4: OBJ is the visual field in object space. IMA is the height of the image point in respect with optical axis. RMS is the root mean square spot radius, i.e., the square root of the distance between each ray and the reference point squared and averaged over all the rays. GEO is the geometric spot radius, i.e., the distance from the reference point to the ray which is farthest away from the reference point, or the radius of the circle centered at the reference point which encloses all the rays. The scanning laser was a 6 mm beam with an 840 nm wavelength. The Airy disk diameter is 66.61 microns which is given by 1.22 times the wavelength (primary wavelength is used if polychromatic) times the F number of the beam and indicates the size of the spot at which the system is diffraction limited. In general, although not limiting, spots with diameters less than the Airy disk diameter are considered optimized and the smaller the spots relative to the Airy disk diameter the better the optimization.

In the configuration illustrated in FIG. 2, lens system 200 illustrates the reflection pass function of compound lens 115 described above. Lens systems that are the same or similar to lens system 200 are used to serve the reflection pass functions of compound lenses 114, 110, and 111 described above. The reflection pass function of lens 111 is essentially the same as the reflection pass function of lens system 200, except that lens 111 directs the wavefront reflected from vertical scanning mirror 112 to horizontal scanning mirror 108. The reflection pass function of lenses 114 and 110 is essentially a mirror image of the reflection pass function of lens system 200.

Figure 3:
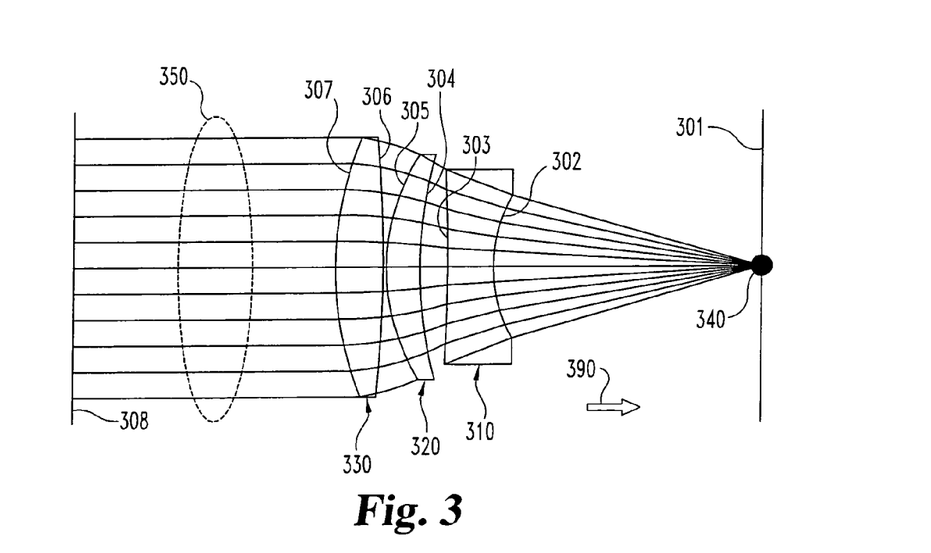
FIG. 3 illustrates an exemplary scanning pass of an exemplary double pass scanning lens system.

FIG. 3 illustrates an exemplary scanning pass of an exemplary DPS lens system 300 with scanning laser beams 350 traveling generally in the direction indicated by arrow 390. In some embodiments scanning laser beams 300 are provided in series over in time. In some embodiments scanning laser beams 300 are provided in parallel. Lens system 300 has the same or similar characteristics as described above for lens system 200 and corresponding features of lens system 300 are labeled with numerals corresponding to those used in FIG. 2 increased by 100. Lenses 310, 320 and 330 are operable to direct light waves 350 to a spot 340 on pupil plane 301 of a patient's eye. Lens system 300 is operable to produce a pupil plane spot with an RMS spot radius of 31.620 microns, a maximum geometric radius of 59.104 microns, and an Airy disk radius of 3.677. Lens system 300 illustrates the scanning pass function of compound lens 115 described above. Lens systems that are the same or similar to lens system 300 are used to serve the scanning pass functions of compound lenses 113, 114, and 123 described above. The scanning pass function of lens 111 is essentially the same as the function of lens system 300, except that lens 111 directs scanning laser beams from lens 110 to vertical scanning mirror 112. The function of lenses 114 and 110 is essentially a minor image of the scanning pass function of lens system 300.

Figure 4:
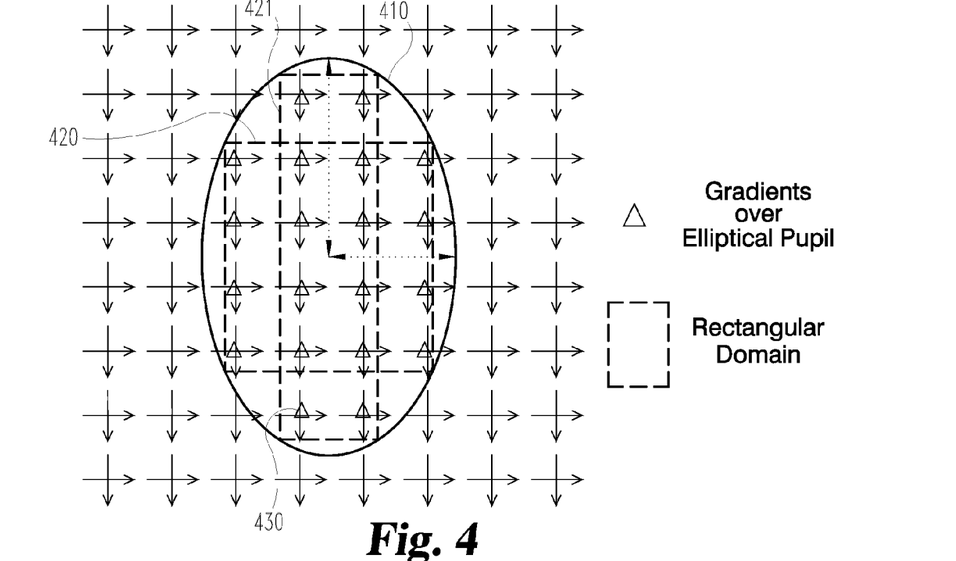
FIG. 4 illustrates an exemplary wavefront reconstruction method for an irregular pupil.

FIG. 4 illustrates an exemplary wavefront reconstruction method within an irregular pupil, for example, an elliptical or oval pupil. Irregular pupils result from off axis measurements such as off-axis wavefront aberration measurements for oblique lines of sight. In the case of scanning Hartmann Shack wavefront sensor system the sampled centroid image formed by the HSWS lenslet array is also irregular and the derived wavefront gradients (slopes) are also defined over this irregular area. As illustrated in FIG. 4, for the gradient data measured within irregular pupil 410, a series of rectangular pupils such as rectangular pupils 420 and 421 are dynamically defined to exhaustively cover the measured gradients such as gradient 430 within the irregular pupil 410. The wavefront defined over each individual rectangular domain from the corresponding gradient data is determined by integrating the measured wavefront gradients to retrieve the corresponding wavefront in the frequency domain with a Fourier transformation. The gradients in the space domain are first transformed to the gradient spectrum in the frequency domain. The gradient spectrum is then passed through a derived integral filter. The filtered spectrum is equivalent to the wavefront spectrum, based on which the wavefront could be retrieved via inverse Fourier transformation. Wavefronts obtained from the different rectangular pupils are used to reconstruct the wavefront over the irregular pupil.

Figure 5:
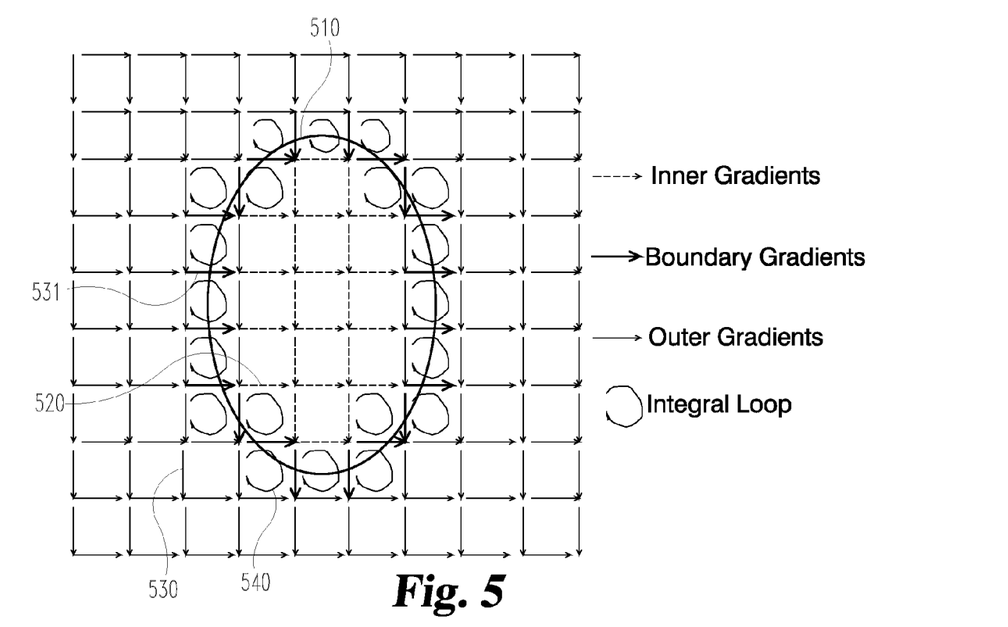
FIG. 5 illustrates an exemplary wavefront reconstruction method for an irregular pupil.

FIG. 5 illustrates an exemplary wavefront reconstruction method for an irregular pupil, for example, an elliptical or oval pupil, using a boundary method based on Fourier series expansion. The boundary method interpolates the gradients beyond irregular pupil 510 to a larger rectangular pupil. Beyond the irregular pupil 510, there are two types of unknown gradients which can be interpolated in different manners. Gradients entirely outside the boundary of the irregular pupil 510, such as gradient 530, can be defined as 0. Boundary gradients lying across boundary of irregular pupil 510, such as gradient 531 can be interpolated using loop integrals such as loop integral 540 to satisfy the Cauchy Integral Theorem via a least square fitting method or another fitting method. Once the extended rectangular pupil is filled with gradients, the techniques described above can be used to retrieve the wavefront over the extended rectangular pupil.

Figure 6:
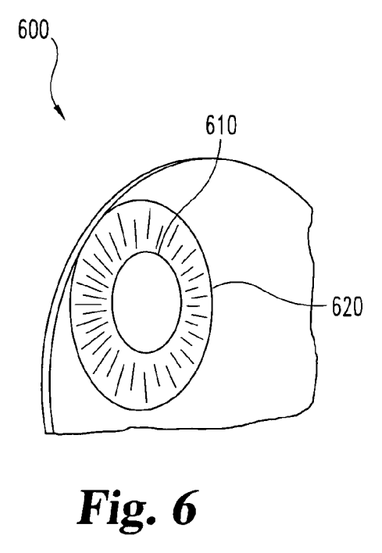
FIG. 6 illustrates a patient's eye viewed from an oblique angle.

FIG. 6 illustrates a patient's eye 600 viewed from an oblique angle where the pupil 610 bounded by iris 620 of eye 600 is elliptical.

Figure 7:
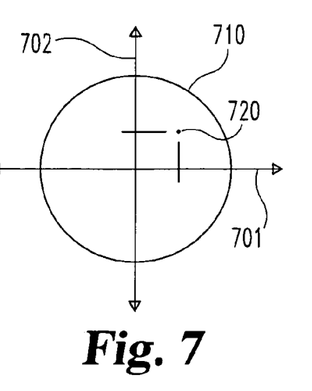
FIG. 7 illustrates an iris coordinate system for a patient's eye.

FIG. 7 illustrates an iris coordinate system 700 for eye 600 which includes axis 701 (the $x_{iris}$ axis) and axis 702 (the $y_{iris}$ axis). In iris coordinate system 700 pupil 710 is circular and points such point 720 can be defined in terms of $x_{iris}$ and $y_{iris}$ values.

Figure 8:
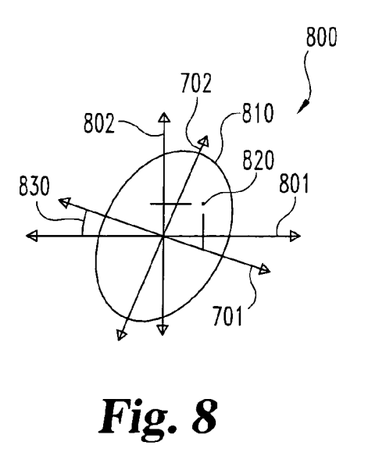
FIG. 8 illustrates an irregular pupil coordinate system for a patient's eye.

FIG. 8 illustrates an irregular pupil coordinate system 800 for eye 600. When viewed from an oblique angle (line of sight) such as line of sight 950 in FIG. 9, the entrance pupil 810 becomes elliptical. A point 820 can be defined in terms of values on x axis 801 and y axis 802 which are offset from axis 701 and 702 by an angle θ (labeled 830). The mathematical linear mapping relation between point 720 and point 820 is given by Equation 1 below. By mapping the oval entrance pupil onto the circular aperture of the eye's iris, all of the wavefront aberration data put onto a common basis needed to construct the model. Otherwise every scanning angle would produce data defined over a different elliptical domain, thereby making the data mutually incommensurate.

Figure 9:
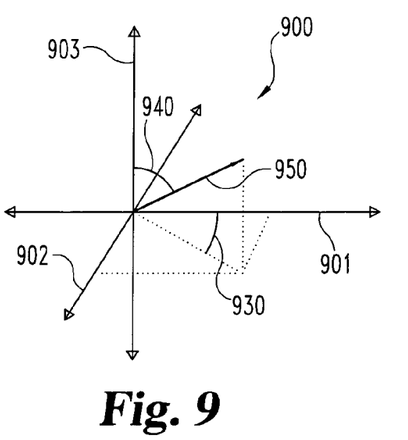
FIG. 9 illustrates a coordinate system with a directional line of sight vector for a patient's eye.

FIG. 9 illustrates a coordinate system 900 with a directional line of sight vector 950 for eye 600. Vector 950 has an angular eccentricity ϵ (labeled 940) relative to the z axis 903 and is angled relative to the x axis 901 in the iris plane defined by x axis 901 and y axis 902 by an angle θ (labeled 930). Thus, there is a relationship among FIGS. 7, 8, and 9 in that entrance pupil 810 of FIG. 8 is the image formed by the iris aperture 710 of FIG. 7. When viewed along a particular line-of-sight 950 in FIG. 9, the entrance pupil 810 becomes elliptical.

Figure 10:
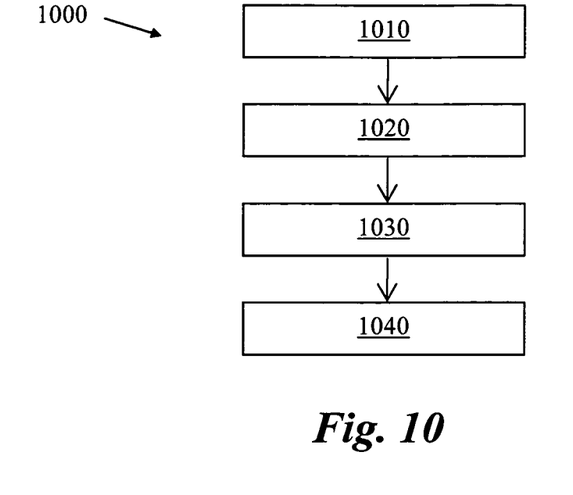
FIG. 10 illustrates an exemplary process for modeling a patient's eye and determining an ophthalmic prescription for a patient's eye.

FIG. 10 illustrates an exemplary process 1000 for modeling a patient's eye and determining a corrective ophthalmic prescription for the patient's eye over a large field of view. Operation 1010 provides a model eye which includes optical parameters and anatomical parameters. A number of model eyes may be provided, for example, general wide angle schematic eyes such as a multi-surface model eye or a GRIN model eye which are obtained from statistical anatomic data can be provided. A model eye may be provided by incorporating ocular structural parameters obtained from a number of techniques, for example, cornea topography, IOL master, ultrasonic techniques, MRI, and/or other techniques.

Operation 1020 transforms peripheral optical characteristics along oblique lines of sight from the pupil plane to the iris plane. In some embodiments, the peripheral optical characteristics are off-axis wavefront aberration measurements which can be obtained using a Hartman-Shack wavefront sensor system, for example, system 100 described above, using laser ray tracing, or using other systems instruments and techniques. In some embodiments, the measured peripheral optical characteristics are other off-axis optical characteristics. Peripheral optical characteristics measured along an oblique line of sight, for example vector 950 illustrated in FIG. 9 are initially defined within an irregular pupil coordinate system, for example, coordinate system 800 shown in FIG. 8 or another elliptical or oval pupil coordinate system. A transformation from the irregular pupil coordinate system to the iris coordinate system is performed in accordance with Equation 1:

$$\begin{pmatrix} x_{iris} \\ y_{iris} \end{pmatrix} = \begin{pmatrix} \cos\theta & \sin\theta \\ -\sin\theta & \cos\theta \end{pmatrix}^{-1} \begin{pmatrix} \cos\varepsilon & 0 \\ 0 & 1 \end{pmatrix}^{-1} \begin{pmatrix} \cos\theta & -\sin\theta \\ \sin\theta & \cos\theta \end{pmatrix}^{-1} \begin{pmatrix} x_{pupil} \\ y_{pupil} \end{pmatrix}$$

The transformed wavefront aberrations ($x_{iris}$, $y_{iris}$) defined on the iris coordinate frame according to Equation 1 for an oblique line of sight (θ, ϵ) may be denoted $W_{iris}^{measurement}$ ($x_{iris}, y_{iris}, \theta_i, \epsilon_i$). Other embodiments may represent wavefront information defined over a circular iris pupil in terms of Zernike Polynomials or Fourier Polynomials.

Operation 1030 provides an optimization goal for the model eye in the form of a Merit function.

Exemplary embodiments provide a Merit function which accounts for the relationship between the optical parameters of a model eye and measured optical characteristics of a patient's eye, for example, functions which measure the similarity or difference between the two. In exemplary embodiments the Merit function also accounts for a relationship between the anatomical parameters of the model eye and measured anatomical characteristics of a patient's eye, for example, functions which measure the similarity of difference between the two. In an exemplary embodiment the optical part of the Merit function represents the similarity between measured off-axis wavefront aberrations along oblique lines of sight and those that are predicted by a model or simulation. Model or simulation predicted off-axis wavefront aberrations can be obtained, for example, via inverse ray-tracing a parallel beams into the model eye from along the same line of sight. Model predicted wavefront aberration along a specific line of sight ($\theta_i, \epsilon_i$) can be represented as $W_{iris}^{model}$ ($x_{iris}, y_{iris}, \theta_i, \epsilon_i, \vec{M}$) where $\vec{M}$ is a vector of anatomical parameters of the model eye, for example, the anterior cornea curvature posterior cornea curvature, anterior lens curvature, posterior lens curvature, retina curvature, anterior chamber thickness, lens thickness, posterior chamber thickness, cornea thickness and/or alternate or additional anatomical parameters.

A number of functions can be used to assess the similarity or fit between measured peripheral optical characteristics such as $W_{iris}^{measurement}(x_{iris}, y_{iris}, \theta_i, \epsilon_i)$ and those predicted by a model such as $W_{iris}^{model}(x_{iris}, y_{iris}, \theta_i, \epsilon_i, \vec{M})$. For example, the similarity can be determined according to Equation 2:

$$Merit_{optical}(\vec{M}) = \frac{\sum_{i=1}^{N} RMS(W_{iris}^{model}(x_{iris}, y_{iris}, \theta_i, \varepsilon_i, \vec{M}) - W_{iris}^{measurement}(x_{iris}, y_{iris}, \theta_i, \varepsilon_i))}{N}$$

In Equation 2 $\vec{M}$ is a vector of anatomical parameters of a model eye, for example a five-surface model eye can be represented as $(r_{AC}, r_{PC}, r_{AL}, r_{PL}, r_R, t_1, t_2, t_3)$ where $(r_{AC}, r_{PC}, r_{AL}, r_{PL}, r_R)$ represent the curvature of multiple ocular surfaces (in this example, the anterior cornea, posterior cornea, anterior lens, posterior lens, and retina) and $(t_1, t_2, t_3)$ represent the thickness of different ocular components (in this example, the anterior chamber, lens, posterior chamber); RMS is a function to calculate the root-mean-square of the given wavefront or wavefront difference; $(x_{iris}, y_{iris})$ is the iris coordinate on which a wavefront is defined; $(\theta_i, \epsilon_i)$ is the line of sight for the i'th measurement; and N is the total number of measurements. In Equation 2, when the model eye models the measured off-axis aberrations along the multiple lines of sight with absolute fidelity, the value of $Merit_{optical}$ is zero although it should be understood that optimizations include near-zero, small, and minimized values as well as zero values. When there is a mismatch between the measured off-axis aberration and theoretical prediction, the function $Merit_{optical}$ measures the mismatch in a monotonic and consistent manner and can be quantified if desired.

Additional embodiments utilize a number of different Merit functions. In some embodiments functions other than RMS are used, for example, least squares fitting techniques, additional paraxial curvature matching techniques, equivalent quadratic fitting techniques, standard deviation of wavefront fitting techniques, peak-valley fitting techniques, RMS fitting techniques, pupil fraction for wavefront (critical pupil) fitting techniques, pupil fraction for wavefront (tessellation) fitting techniques, pupil fraction for slope (tessellation) fitting techniques, pupil fraction for slope (critical pupil) fitting techniques, average blur strength fitting techniques, pupil fraction for curvature (tessellation) fitting techniques, pupil fraction for curvature fitting techniques, 50% width (min) fitting techniques, equivalent width (min) fitting techniques, 2nd moment square root (min) fitting techniques, half width at half height (arcmin) fitting techniques, correlation width (min) fitting techniques, Strehl ratio in space domain fitting techniques, light in the bucket (norm) fitting techniques, standard deviation of intensity (norm) fitting techniques, entropy (bits) fitting techniques, neural sharpness (norm) fitting techniques, visual Strehl in space domain fitting techniques, cutoff spatial frequency for rMTF (c/d) fitting techniques, area of visibility for rMTF (norm) fitting techniques, cutoff spatial frequency for rOTF (c/d) fitting techniques, area of visibility for rOTF (norm) fitting techniques, Strehl ratio for OTF fitting techniques. OTF vol/MTF vol fitting techniques, visual Strehl ratio for OTF fitting techniques, CS*OTF vol/CS*MTF vol fitting techniques, Strehl ratio for MTF fitting techniques, visual Strehl ratio for MTF fitting techniques, and curvature fit Fitting techniques, standard deviation, statistical median, variance, pupil fraction, comparison of point spread functions, or other functions.

In some embodiments the measured and predicted off-axis wavefronts aberration defined over the circular iris pupil can be fitted with the Zernike polynomials or Fourier polynomials and the Merit function compares the fitted coefficients between the measurements and prediction. In some embodiments the Merit function compares the image quality metrics derived from off-axis wavefront aberration. In some embodiments different weighting factors can be assigned for each oblique line of sight to stress the relative weights of the desired match of the individual optical quality along the specific line of sight, for example, if heavier weight is assigned to the central line of sight, the optimized model eye will have higher priority to mimic the central optical quality in terms of accuracy. In some embodiments different weighting factors can be assigned to stress the relative weights of the desired match of specific aberration component (for example, a defocus term) along specific lines of sight, for example, if heavier weight is assigned to the spherical aberration of the wavefront aberration along the central line of sight, the optimized model eye will have higher priority to mimic the foveal spherical aberration in terms of accuracy. In some embodiments, the Merit function involves the combinations of foregoing techniques and/or other techniques.

The anatomical part of the Merit function represents the anatomical structural similarity between the eye model and a statistical average from the population or actual measurements of a patient's eye. Anatomical parameters can be represented in a vector format such as $\vec{M}$, and anatomical similarity can be expressed by various distance measures (for example, Euclidean distance) as in Equation 3:

$$Merit_{anatomical}(\vec{M}) = \|\vec{M} - \vec{M}_{statistic}\|_{distance}$$

In other embodiments measured information of a patient's eye may be utilized instead of statistical information. In some embodiments Equation 4 may be used:

$$Merit_{anatomical}(\vec{M}) = \|\vec{M} - \vec{M}_{statistic}\|_{distance}$$

An exemplary overall Merit function representing an optimization goal for the model eye can be obtained by combining Equation 2 and Equation 3. An exemplary overall Merit function which measures the peripheral optical similarity and anatomical similarity of a model eye to measurements of patient's eye is expressed in Equation 4:

$$Merit(\vec{M}) = Merit_{optical}(\vec{M}) + Merit_{anatomical}(\vec{M})$$

The smaller the value of the Merit function of Equation 4, the more similar the modeled optical characteristics are to the measured optical characteristics and to the anatomical structure of the measured eye.

Operation 1040 minimizes the overall Merit function to optimize the model eye to the patient's eye. Once the optimization goals are defined numerically as Merit function, an optimized model eye $\vec{M}_{optimal}$ can be obtained by minimizing the Merit function, for example, as defined in Equation 4 via various practical approaches including, for example, simulated annealing, neural network, case-based reasoning, iterative adjustment of model parameters and others.

Figure 11:
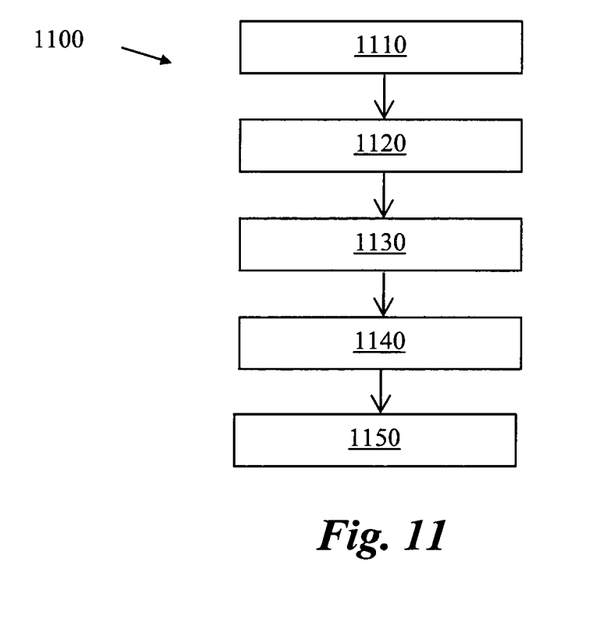
FIG. 11 illustrates an exemplary process for determining an ophthalmic prescription for a patient's eye.

FIG. 11 illustrates an exemplary process 1100 for determining an ophthalmic prescription for the peripheral visual field of a patient's eye as well as the central visual filed. Process 1100 may be used to determine a variety of ophthalmic prescriptions, for example, a spectacle lens, a contact lens, an interocular lens, or a surgical anatomical modification such as a LASIK corneal ablation prescription or other surgical prescription, or any other device or procedure that adds a refractive component to a patient's ocular system. Process 1100 may also determine combinations of the foregoing prescriptions.

Operation 1110 provides a model eye. In an exemplary embodiment, the model eye is the model eye from process 1000 described above which has been adjusted or optimized to match measured characteristics of the patient's eye. In other embodiments, the model eye is another type of model eye, for example, a model eye derived from statistical data.

Operation 1120 defines a desired optical quality to be corrected along multiple lines of sight. Some embodiments define the desired central and peripheral optical quality to be diffraction limited. Some embodiments define the desired corrected eye have a relative myopia pattern in peripheral vision to slow/control the patient's myopia progression.

Operation 1130 transforms optical characteristics along oblique lines of sight from the pupil plane to the iris plane. Operation 1130 may use the same technique as in operation 1020 described above. The transformed off-axis wavefront aberration maps in the iris coordinate frame along the specific line of sight is written as $W_{iris}^{desired}(x_{iris}, y_{iris}, \theta_i, \epsilon_i, \vec{M})$ where $(x_{iris}, y_{iris})$ are the iris reference coordinates and $(\theta_i, \epsilon_i)$ is the direction of an oblique line of sight.

Operation 1140 provides a Merit function that numerically represents the optimization goal. In some embodiments the optimization goal is to find an optimal ophthalmic correction design (for example, one or more refractive surfaces) that effectively changes the wearer's peripheral optical quality and central optical quality and to constrain the ophthalmic correction design within the physical limitations for the contact lens, for example, thickness, refractive index or other limits on the physical characteristics of the contact lens.

In exemplary embodiments the Merit function includes a first part which compares the desired off-axis wavefront aberrations along multiple lines of sight with those obtained from simulation with the model eye, for example, by inverse ray-tracing the model eye fitted with ophthalmic designs. Other alternative strategies described in connection with operation 1030 above may also be applied here. The priority of correction of the optical quality may vary with the angle of the line of sight. A weighting factor is assigned to the similarity measure of each line of sight. Larger weighting factor corresponds to the higher priority the match of the optical quality along the specific line of sight. For example, in embodiments where correction of foveal optical quality is assigned the first priority the weighting factor will be largest for the line of sight across the fovea. In some embodiment the Merit function is as described in Equation 5:

In Equation 5, $\vec{M}_{design}$ includes the ophthalmic design's physical structural parameters. For example it can be a vector such as $(r_{AS}, c_{AS}, t)$ for a contact lens design, where $r_{AS}$ represents the contact lens' radius of curvature, $c_{AS}$ is conic constant, and t represents contact lens' thickness; $weight_i$ is a weighting factors for each off-axis wavefront along the i'th line of sight; RMS is a function to calculate the root-mean-square of the given wavefront or wavefront difference; $(x_{iris}, y_{iris})$ is the iris coordinate on which a wavefront is defined; $(\theta_i, \epsilon_i)$ is the line of sight for the i'th measurement; and $$\sum_{i=1}^{N}$$

$weight_i$ is the sum of the weighting factors for N lines of sight.

In exemplary embodiments the Merit function includes a second part, $Merit_{PhysContra\,int}(\vec{M}_{design})$ which limits the ophthalmic correction design within its physical constraint such as fabrication limitations and fitting limitation of ophthalmic design with the human eye. For example, certain materials fabrication limitations make it infeasible to make 10 mm-diameter Gas-permeable contact lens with central thickness smaller than 0.2 mm due to the material brittleness. In another example, the diameter of an interocular lens is limited within a certain range in order to be fit with the patients' eye. A number of functions may be used to numerically represent the physical constraint(s). Exemplary functions satisfy two conditions (1) if all the structural parameters of the ophthalmic design are within the structural constraint, then value of the Merit function is zero or very close to zero and (2) if there are some structural parameter overruns the physical constraint, the Merit function has to be able to measure the extent of such overrun. Some embodiments utilize the Heaviside step function to construct a Merit function. For example, limiting the radius to 3 mm can be formulated as $(r-3)\times H(r-3)$ where r is the radius and H is the Heaviside step function. In embodiments which utilize the first and second components of the Merit function described above, the overall Merit function that numerically represents the optimization goal is given by Equation 6:

$$Merit(\vec{M}_{design}) = Merit_{PhysContra\,int}(\vec{M}_{design}) + Merit_{optical}(\vec{M}_{design}).$$

Operation 1150 adjusts parameters of the corrective feature to the optimization goal by minimizing the Merit function. Since the Merit function numerically represents the optimization goal, adjusting the ophthalmic correction design to meet the optimization goal can be accomplished by finding a design parameter vector $\vec{M}_{design}^{optimal}$ that corresponds to the minimum value of the Merit function. Operation 1150 can utilize the same or similar techniques as in operation 1040 described above to accomplish this and determine a prescription.

$$Merit_{optical}(\vec{M}_{design}) = \frac{\sum_{i=1}^{N} weight_i \times RMS(W_{iris}(x_{iris}, y_{iris}, \theta_i, \epsilon_i, \vec{M}_{design}) - W_{iris}^{desired}(x_{iris}, y_{iris}, \theta_i, \epsilon_i))}{\sum_{i=1}^{N} weight_i}.$$

Some examples involve the optimization of a surgical procedure such as a LASIK procedure. To correct a patient's central vision, the LASIK procedure essentially manipulates the shape of anterior cornea surface by using an excimer laser to photoablate a portion of the cornea subjacent a flap created in the cornea. To optimize a LASIK procedure, a model eye such as one of the aforementioned model eyes is provided and the pre-LASIK shape of the anterior cornea is set as a variable parameter. The optimized LASIK procedure is effective to correct the central vision, and enhance the wearer's peripheral optical quality or serve as a myopia inhibitor that introduces relative myopia pattern into myopia wearer's eye.

In one myopia inhibition example, a fixed wide angle schematic eye was chosen as a design template under the wavelength of 543 nm. The axial length of this model eye was modified to introduce a −2D on-axis defocus (EP=6 mm). Procedures 1000 and/or 1100 can be applied to find the optimal cornea shapes. The Pre-LASIK cornea shape of the model eye was a sphere according to Equation 7:

$$y_{PreLASIK}(x) = \frac{x^2/7.82}{1+\sqrt{1-\frac{x^2}{7.82^2}}}$$

To correct the central myopia and to introduce the peripheral myopia pattern to this myopia model eye, the optimal Post-LASIK cornea shape is a conic section according to Equation 8:

$$y_{PostLASIK}(x) = \frac{x^2/8.01}{1+\sqrt{1-\frac{(1.22+1)x^2}{8.01^2}}} + 0.019$$

where the apical radius of curvature R=8.01, the conic constant=1.22 and the optical zone radius=4.03.

Figure 12:
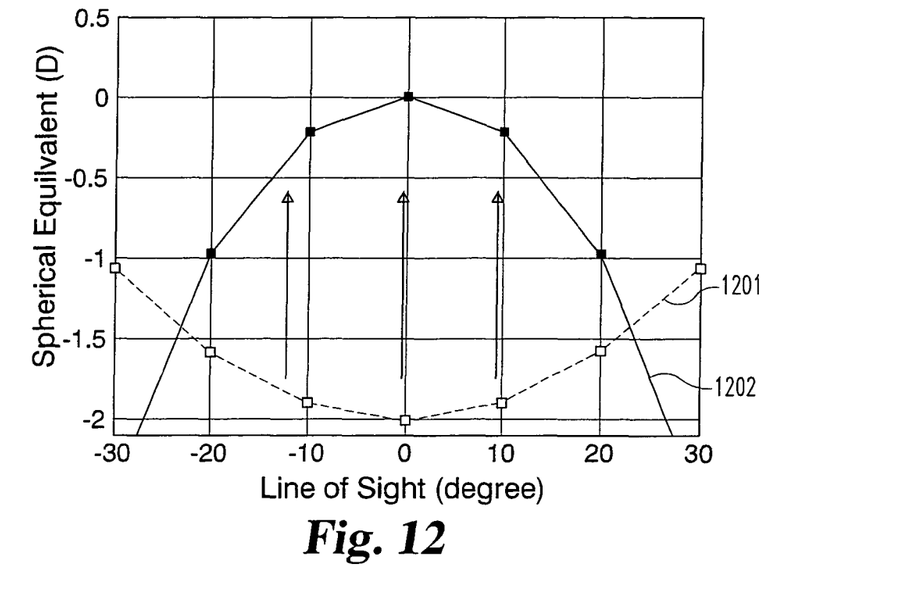
FIGS. 12 and 13 illustrate examples of LASIK prescriptions determined in accordance with an exemplary process for determining a corrective ophthalmic prescription for a patient's eye.

During the LASIK procedure to manipulate the cornea shape, the surgeon uses the laser to photoablate corneal tissue. This ablation profile corresponds to the difference between PRE-LASIK and Post-LASIK cornea profiles ($y_{PostLASIK}(x) - y_{PreLASIK}(x)$). The corresponding peripheral optical quality pattern is illustrated in FIG. 12 which show a graph of uncorrected spherical equivalents 1201 and corrected spherical equivalents 1202 as a function of the angle of the line of sight. As shown by curve 1202, the optimized cornea shape introduced a relative myopia pattern to the patient's peripheral visual field.

Figure 13:
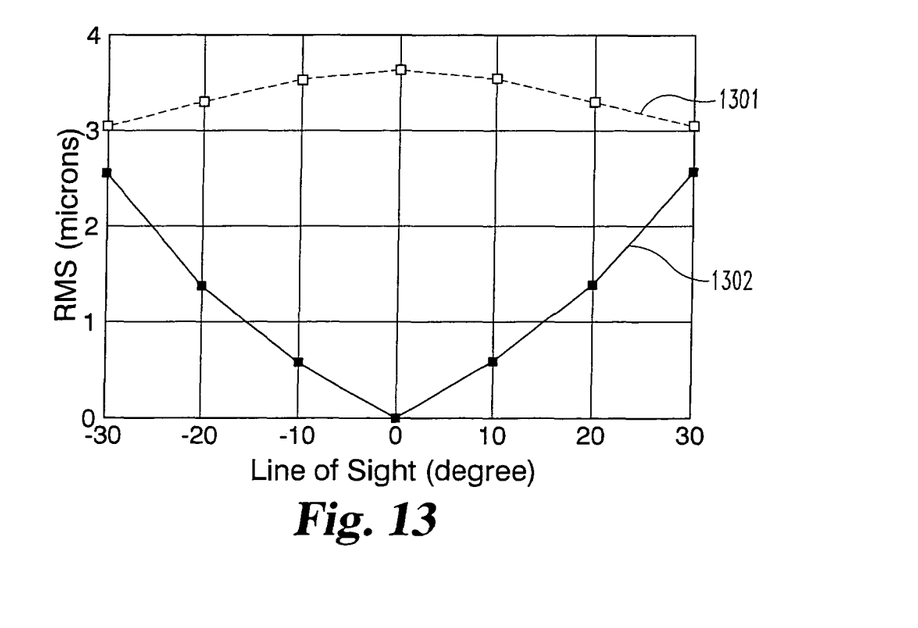

In one example of improving peripheral image quality, an optimal post-LASIK cornea shape to improve the peripheral optical qualities is determined in accordance with Equation 9:

$$y_{PostLASIK}(x) = \frac{x^2/7.99}{1+\sqrt{1-\frac{(-0.52+1)x^2}{7.99^2}}} + 0.075$$

where the apical radius of curvature R=7.99 mm, the conic constant −0.52 and the optical zone radius=4.12 mm. FIG. 13 illustrates the uncorrected optical quality 1301 and corrected optical quality 1302. The optimized cornea shape significantly improves the peripheral optical pattern as the smaller RMS for a given line of sight has, the better image quality of that line of sight has.

Some examples involve the optimization of a contact lens design. In the contact lens optimization example, the anterior contact lens surface is fit with a fixed eye model. By applying the procedures described above, an optimal shape (radius and conic constant) of the anterior contact lens surface was found. The optimized contact lens can be designed to enhance the patient's peripheral optical quality or serves as a myopia inhibitor that introduces relative myopia pattern into myopia patient's eye. Examples of correction for model eyes with various levels of myopia (−2D, −4D, or −6D) are presented below. The models included a fixed model eye and an aspheric contact lens whose apical radius of curvature and conic constant of the contact are adjustable parameters represented by vector $\vec{C}L$. The optimization was defined according to the Merit function of Equation 10:

$$\text{Merit}(\vec{C}L) = \text{Merit}_{DesigGoal}(\vec{C}L) + \text{Merit}_{DesignConstraint}(\vec{C}L)$$

and the contact lens shape was modeled in accordance with aspheric Equation 11:

$$9y(x) = \frac{x^2/R}{1+\sqrt{1-\frac{(K+1)x^2}{R^2}}}$$

Figure 14:
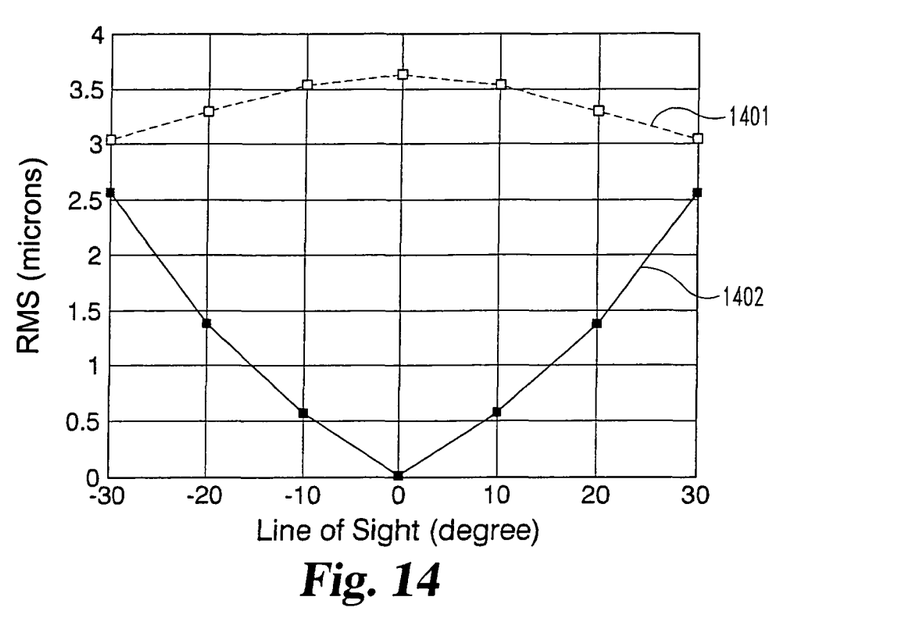
FIGS. 14, 15, 16, 17, 18 and 19 illustrate examples of contact lens prescriptions determined in accordance with an exemplary process for determining a corrective ophthalmic prescription for a patient's eye.
Figure 15:
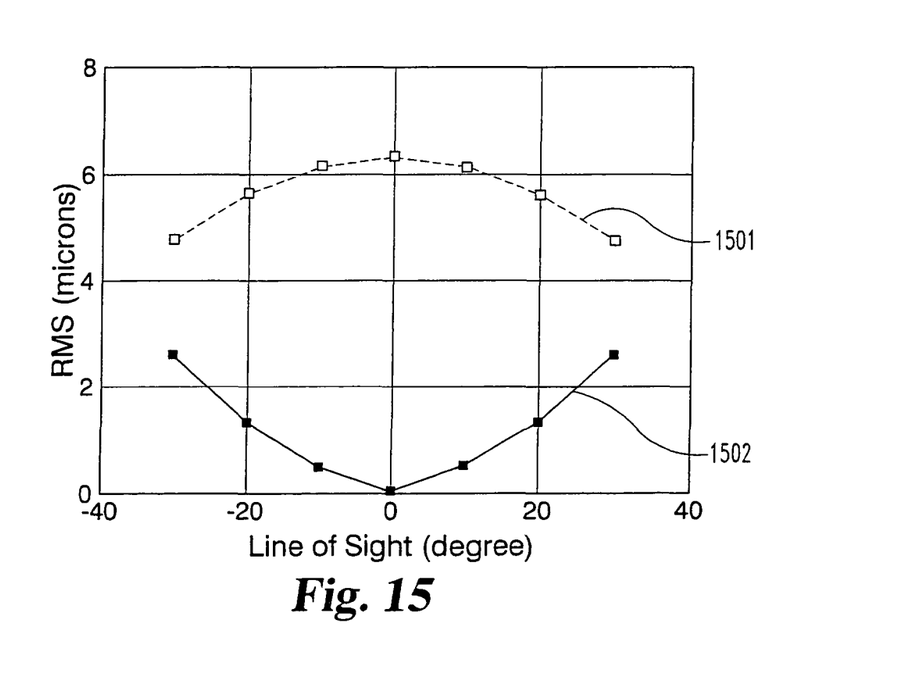
Figure 16:
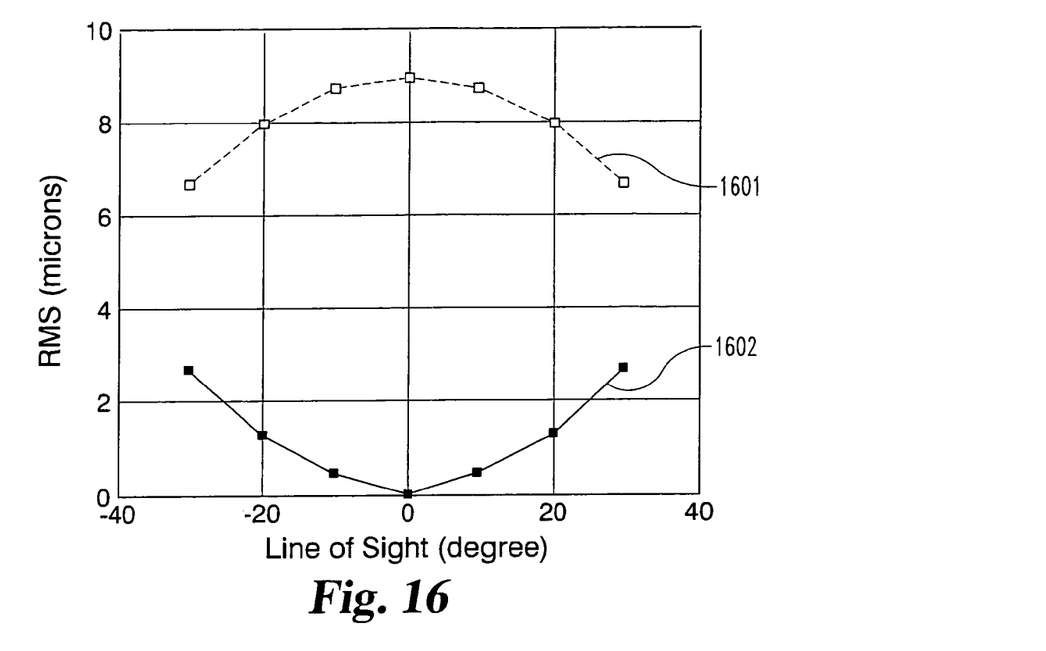

FIGS. 14, 15 and 16 illustrate examples where the optimized contact lens is designed to enhance the patient's peripheral optical quality with −2D, −4D, and −6D myopia, respectively. FIG. 14 shows uncorrected optical quality 1401 and corrected optical quality 1402. FIG. 15 shows uncorrected optical quality 1501 and corrected optical quality 1502. FIG. 16 shows uncorrected optical quality 1601 and corrected optical quality 1602. In all cases, the optimized contact lens shape improves peripheral optical quality.

Figure 17:
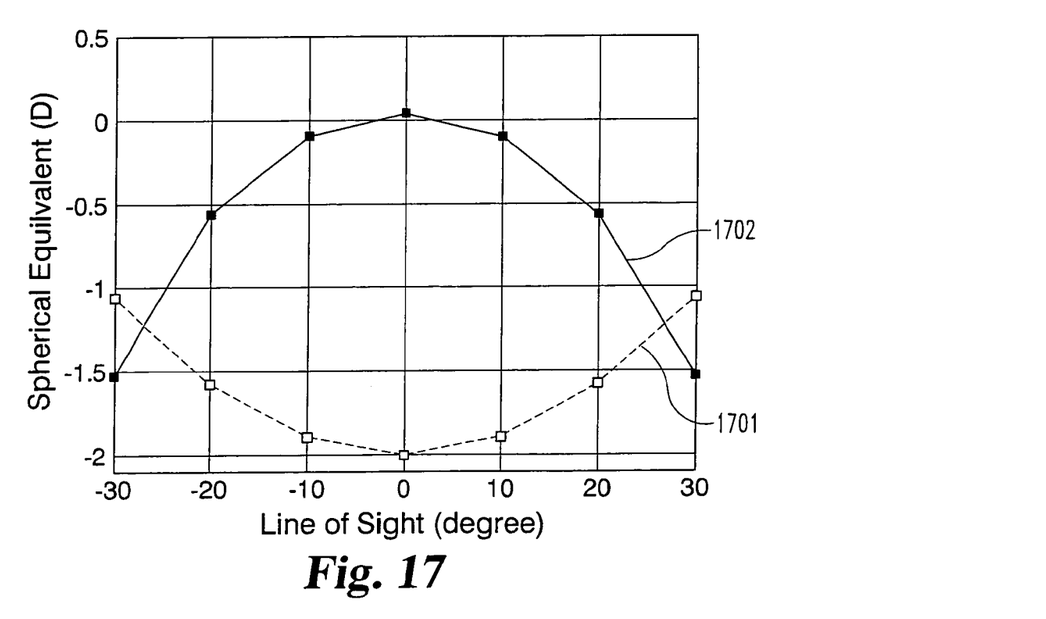
Figure 18:
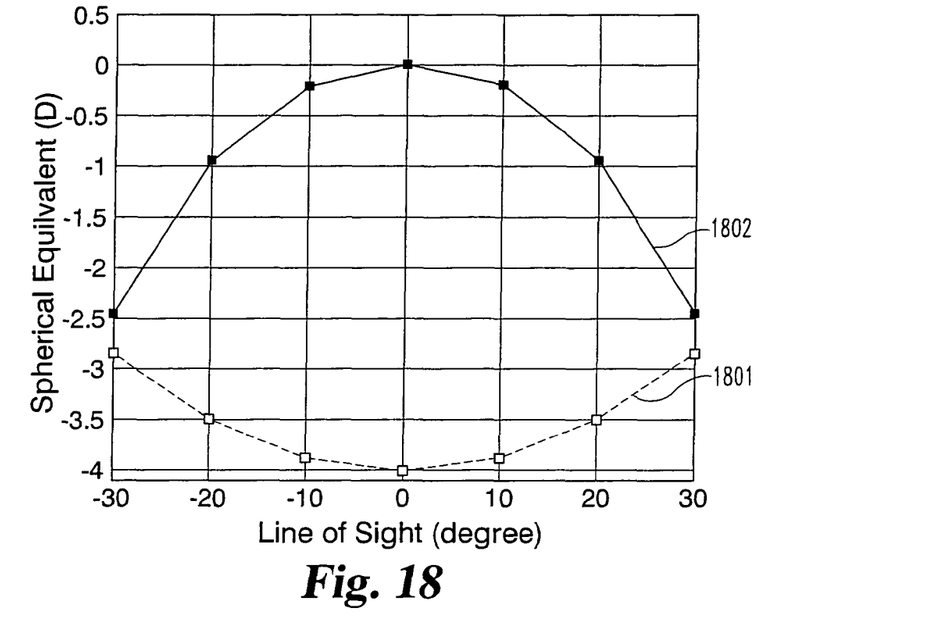
Figure 19:
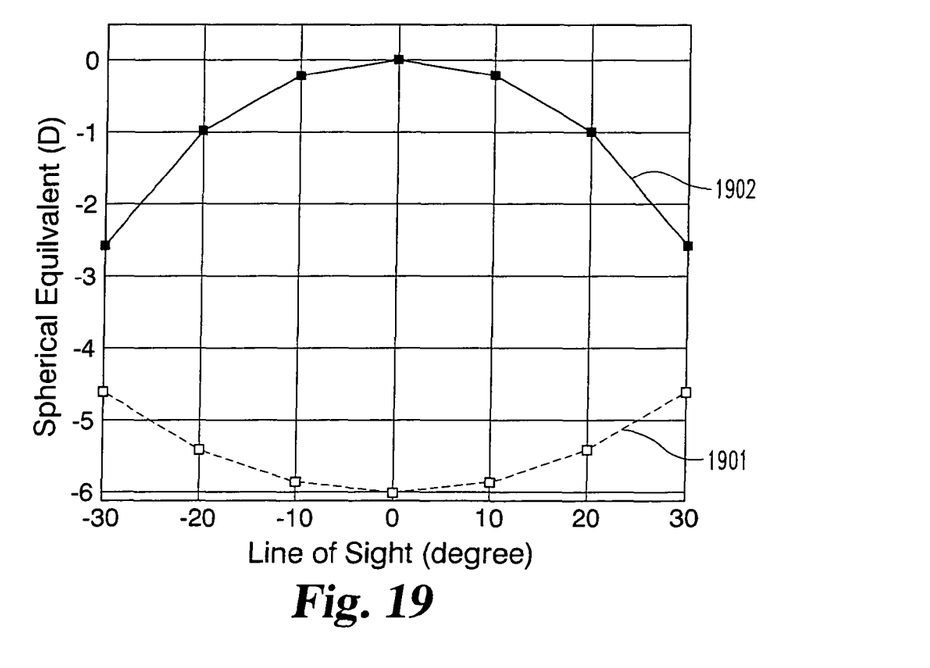

FIGS. 17, 18 and 19 illustrate examples where the optimized contact lens serves as a myopia inhibitor that introduces relative myopia pattern into myopia patient's eye with −2D, −4D, and −6D myopia, respectively. FIG. 17 shows uncorrected optical quality 1701 and corrected optical quality 1702. FIG. 18 shows uncorrected optical quality 1801 and corrected optical quality 1802. FIG. 19 shows uncorrected optical quality 1901 and corrected optical quality 1902. In all cases, the optimized contact lens shape successfully introduce relative myopia pattern into myopia patient's eye.

While exemplary embodiments of the invention have been illustrated and described in detail in the drawings and foregoing description, the same is to be considered as illustrative and not restrictive in character. It shall be understood that only the preferred embodiments have been shown and described and that all changes and modifications that come within the spirit of the invention are to be protected. It shall be understood that the operations of the processes and methods herein may be performed in the exemplary orders described herein and that in other embodiments the order of operations may be varied, operations may be performed in parallel as well as in series and that no limitation on such variations shall be implied unless expressly indicated to the contrary. It shall further be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow.

What is claimed is:

1. An a scanning wavefront aberrometer comprising:
a laser operable to emit a laser beam; a scanning mirror operable to scan the laser beam over at least a +/−15 degree scan; and a double pass scanning lens system comprising a telescopic pair of lenses, wherein each of the lenses within said telescopic pair comprises at least a three component lens, said double pass scanning lens system operable to receive the laser beam from the scanning mirror and direct the laser beam to a spot on a patients entrance pupil plane and operable to receive reflected light from the patient's eye and direct the reflected light to a sensor operable to sense the reflected light; wherein the lens system optically conjugates the center of the scanning mirror with the center of the patient's entrance pupil and optically conjugates an entrance aperture of the sensor with the patient's entrance pupil, the lens system being configured to minimize scanning pass aberration of the laser beam over the range of said at least +/−15 degree scan, and the lens system being configured to minimize reflection pass aberration of light reflected from the eye over the range of said at least +/−15 degree scan.

2. An ophthalmic scanning apparatus according to claim 1 wherein the lens system is configured to minimizes optical aberrations of both the optical conjugation of the center of the scanning mirror with the center of the patient's entrance pupil and the optical conjugation of the entrance aperture of the sensor with the patient's entrance pupil.

3. An ophthalmic scanning apparatus according to claim 1 wherein the lens system is configured to balance the reduction of optical aberrations of the optical conjugation of the center of the scanning mirror with the center of the patient's entrance pupil and the reduction of optical aberrations of the optical conjugation of the entrance aperture of the sensor with the patient's entrance pupil.

4. An ophthalmic scanning apparatus according to claim 1 wherein the lens system is operable to direct reflected light to spots on an image plane having root mean square radii of less than about 3.8 microns over the +/−15 degree scan.

5. An ophthalmic scanning apparatus according to claim 1 wherein the lens system is operable to direct reflected light to spots on an image plane, the spots having diameters smaller the Airy disk diameter of the system.

6. An ophthalmic scanning apparatus according to claim 1 wherein the optical aberration introduced by the lens system is about ⅓ of the dynamic range of the sensor or less.

7. An ophthalmic scanning apparatus according to claim 1 wherein the dynamic range of the sensor minus the optical aberration of the lens system is greater than the optical aberration of the patient's eye.

8. An ophthalmic scanning apparatus according to claim 1 wherein the lens system is operable to direct reflected light to spots on an image plane having root mean square radii of less than about 4 microns over the +/−15 degree scan.

9. An ophthalmic scanning apparatus according to claim 1 wherein the lens system is operable to direct the laser beam to spots on an image plane having diameters less than about 66 microns over the +/−15 degree scan.

10. An ophthalmic scanning apparatus according to claim 1 further comprising a second scanning mirror operable to scan the laser beam over a +/−15 degree scan in a second scanning direction and a second lens system operable to receive the laser beam from the second scanning mirror and direct the laser beam to the first scanning mirror;
wherein the apparatus is operable to optically conjugate the center of the first scanning mirror with the center of the second scanning mirror, to optically conjugate the center of the first scanning mirror and the center of the second scanning mirror with the center of the patient's entrance pupil, and to optically conjugate the entrance aperture of the sensor with the patient's entrance pupil; and
wherein the optical aberrations of both the optical conjugation of the center of the scanning mirror with the center of the patient's entrance pupil and the optical conjugation of the entrance aperture of the sensor with the patient's entrance pupil are minimized.

11. A method comprising: directing a laser beam to a scanning wavefront aberrometer system including scanning mirrors and a double pass scanning lens system comprising a telescopic pair of lenses, wherein each of the lenses within said telescopic pair comprises at least a three component lens; operating the scanning mirrors to scan the laser beam over a horizontal scanning range of at least a +/−15 degrees and a vertical scanning range of at least a +/−15 degrees; directing the laser beam through the double pass scanning lens system to a central spot on a patient's pupil over the horizontal scanning range and the vertical scanning range, the scanning pass aberration of the double pass scanning lens system configured such that the central spot has a root mean square radius of less than about 2 mm; reflecting light through the double pass scanning lens system over the horizontal scanning range and the vertical scanning range from the patient's eye through the system to a sensor, the reflection pass aberration introduced by the lens system configured to provide spots on an image plane having root mean square radii less than about 3.8 microns; and detecting information of optical characteristics of the patient's eye with a sensor; wherein the scanning pass aberration of the laser beam is minimized over said at least +/−15 degree scan, and the reflection pass aberration of reflected light is minimized over said at least +/−15 degree scan.

12. A method according to claim 11 wherein the central spot has a root mean square radius of less than about 600 microns.

13. A method according to claim 11 wherein the central spot has a root mean square radius of less than about 1 mm.

14. A method according to claim 11 wherein the detecting information of optical characteristics of the patient's eye with the sensor includes determining wavefront information for an elliptical or oval pupil.

15. A method according to claim 11 further comprising processing the detected information of optical characteristics of the patient's eye including defining a plurality of rectangular pupils to cover an elliptical or oval pupil, determining wavefront information for the plurality of rectangular pupils, and combining the wavefront information for the plurality of rectangular pupils to determine wavefront information for the elliptical or oval pupil.

16. A method according to claim 11 further comprising processing the detected information of optical characteristics of the patient's eye including interpolating gradients for regions intersecting with a non-circular pupil boundary to define an extended rectangular pupil, transforming gradients of the rectangular pupil to the frequency domain, filtering the transformed gradients, and transforming the filtered gradients to the spatial domain.

17. A method according to claim 11 wherein the system includes a horizontal scanning mirror a first pair of compound double pass scanning lenses, and a vertical scanning mirror and a second pair of compound double pass scanning lenses.

18. An ophthalmic scanning aberrometer apparatus comprising: a laser operable to emit a laser beam; a scanning mirror operable to scan the laser beam over at least a +/−15 degree scan; and a double pass scanning lens system comprising a telescopic pair of lenses, wherein each of the lenses within said telescopic pair comprises at least a three component lens, said double pass scanning lens system operable to receive the laser beam from the scanning mirror and direct the laser beam to a spot on a patient's entrance pupil plane and operable to receive reflected light from the patient's eye and direct the reflected light to a sensor operable to sense the reflected light; wherein the double pass lens system optically conjugates the center of the scanning mirror with the center of the patient's entrance pupil and optically conjugates an entrance aperture of the sensor with the patient's entrance pupil, the lens system being configured to minimize scanning pass aberration of the laser beam over the range of said at least +/−15 degree scan, and the lens system being configured to minimize reflection pass aberration of light reflected from the eye over the range of said at least +/−15 degree scan.

19. An ophthalmic scanning apparatus according to claim 18 wherein the lens system is configured to minimize optical aberrations of both the optical conjugation of the center of the scanning mirror with the center of the patients entrance pupil and the optical conjugation of the entrance aperture of the sensor with the patients entrance pupil.

20. An ophthalmic scanning apparatus according to claim 18 wherein the lens system is configured to balance the reduction of optical aberrations of the optical conjugation of the center of the scanning mirror with the center of the patients entrance pupil and the reduction of optical aberrations of the optical conjugation of the entrance aperture of the sensor with the patients entrance pupil.

* * * * *